United States Patent [19]

Young et al.

[11] Patent Number: 4,759,828
[45] Date of Patent: Jul. 26, 1988

[54] GLUCOSE ELECTRODE AND METHOD OF DETERMINING GLUCOSE

[75] Inventors: Chung C. Young, Weston; Kenneth Gary, Belmont; Handani Winarta, Waltham; Chin-Chun Chen, Wayland, all of Mass.

[73] Assignee: Nova Biomedical Corporation, Waltham, Mass.

[21] Appl. No.: 36,495

[22] Filed: Apr. 9, 1987

[51] Int. Cl.⁴ .................. G01N 27/30; C12Q 1/54
[52] U.S. Cl. .................. 204/1 T; 204/403; 204/415; 435/14; 435/291; 435/817
[58] Field of Search .......... 435/817, 291, 14; 204/1 E, 403, 415; 128/635

[56] References Cited

U.S. PATENT DOCUMENTS

| | | |
|---|---|---|
| 3,098,813 | 7/1963 | Beebe et al. ................. 204/195 |
| 3,539,455 | 11/1970 | Clark ............................ 204/1 T |
| 3,542,662 | 11/1970 | Hicks et al. .................. 204/195 |
| 3,575,836 | 4/1971 | Sternberg .................... 204/195 |
| 3,707,455 | 12/1972 | Derr et al. ................... 204/195 |
| 3,718,563 | 2/1973 | Krull et al. .................. 204/195 |
| 3,838,033 | 9/1974 | Mindt et al. ................. 204/195 |
| 3,869,354 | 3/1975 | Montalvo, Jr. .............. 204/1 T |
| 3,979,274 | 9/1976 | Newman ..................... 204/195 |
| 4,073,713 | 2/1978 | Newman ..................... 204/195 |
| 4,220,503 | 9/1980 | Johnson ...................... 204/1 T |
| 4,356,074 | 10/1982 | Johnson ...................... 204/195 |
| 4,404,066 | 9/1983 | Johnson ...................... 204/1 T |

FOREIGN PATENT DOCUMENTS

| | | | |
|---|---|---|---|
| 0079502 | 5/1983 | European Pat. Off. | ........... 204/403 |
| 0080601 | 6/1983 | European Pat. Off. | ........... 204/403 |
| 0185153 | 9/1985 | Japan | ........... 204/403 |

OTHER PUBLICATIONS

Wingard Jr., et al., *J. of Biomedical Materials*, "Immobilized Enzyme Electrodes for the Potentiometric Measurement of Glucose Concentration: Immobilization Techniques and Materials", vol. 13, (1979), pp. 921-935.

Iriyama et al., *Jikeikai Medical Journal*, "A Convenient Method for Preparing a Glucose Sensor", vol. 29, (1982), pp. 889-346.

Clark et al., *Annals of the N.Y. Acad. of Sci.*, "Electrode Systems for Continuous Monitoring in Cardiovascular Surgery", vol. 102, pp. 29-45, (10/31/62).

*Primary Examiner*—G. L. Kaplan

[57] ABSTRACT

An electrode assembly for polarographic assay of glucose in solution having a laminated membrane, the outer membrane being from 1 to 20 μm thick and having a pore size of 10 to 125 Å, the inner membrane having a thickness of 2 to 4 μm, and bonded to the outer membrane with immobilized glucose oxidase. Rapid assays are carried out by measuring the current difference before equilibrium is attained and at least 5 seconds after initial contact of sample with the outer membrane.

10 Claims, 3 Drawing Sheets

GLUCOSE ELECTRODE AND METHOD OF DETERMINING GLUCOSE

This invention relates to an improved enzyme electrode assembly including a laminated membrane for assay of glucose in solution and to a high speed method for glucose solution assay, particularly for use in assay of undiluted whole blood or serum.

BACKGROUND OF THE INVENTION

It has previously been proposed to employ enzyme electrodes having laminated membranes for assaying glucose as described for example in Clark U.S. Pat. No. 3,539,455; Newman U.S. Pat. Nos. 3,979,274 and 4,073,713; Johnson U.S. Pat. Nos. 4,220,503, 4,356,074 and 4,404,066; and Japanese Patent Application publication No. 60-185153. Such enzyme electrode assays of glucose involve measurement of the enzyme-catalyzed oxidation of glucose in accordance with the following reaction:

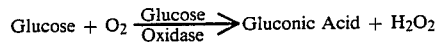

$$\text{Glucose} + O_2 \xrightarrow{\text{Glucose Oxidase}} \text{Gluconic Acid} + H_2O_2$$

The enzyme, glucose oxidase, is interposed and immobilized between two membranes, the first or outer of which comes into contact with the sample to be assayed and permits access of glucose and of oxygen to the enzyme from the sample while restricting the passage of proteins, red blood cells, and other macromolecules, and the second of which is in close relationship with the face of the sensor electrode and permits access of hydrogen peroxide to the electrode while at the same time excluding passage of interfering substances having a molecular weight greater than about 250, e.g., ascorbic acid, uric acid, and salicylic acid. In practice, the sample to be assayed, which contains both glucose and oxygen, is brought into contact with the outer face of the first or outer membrane. Diffusion of the sample through the membrane into contact with the immobilized enzyme leads to the reaction set forth above, and diffusion of the resulting hydrogen peroxide through the second or inner membrane into contact with the sensor electrode causes development of an electrical current which can then be read by conventional means, thus enabling determination of the glucose by calculations based upon similar measurements made on standard solutions containing known concentrations of glucose. The membrane-covered electrode face can be brought into contact with the sample solution either by immersing it in a bath of the sample or by providing a flow cell or chamber through which the sample is passed across the outer face of the first or outer membrane. However, glucose assays conducted as in the prior art have lacked accuracy in the case of solutions having high concentrations of glucose, as are often found for example in undiluted whole blood or serum. It has consequently been the practice to dilute such high-concentration samples by a suitable amount of buffer before assay. The dilution step is time-consuming and is itself an additional source of possible error.

It has now been found that the thickness and pore size of the first or outer membrane in contact with the sample is critical for achieving consistent and accurate measurements, particularly when the samples to be assayed have a high concentration of glucose. The membranes of the prior art have generally been so highly permeable to the passage of glucose that, particularly in the case of samples having high concentrations of glucose, the amount of glucose coming into contact with the immobilized enzyme exceeds the amount of oxygen available. Consequently, the oxygen concentration is the rate-limiting component of the reaction rather than the glucose concentration, so that the accuracy of the glucose assay is destroyed. Equally critical is the thickness and pore size of the second or inner membrane, which must be sufficiently permeable to permit passage of the hydrogen peroxide to the electrode surface as rapidly as it is formed, but which should not permit the ready passage of potential interfering substances. Retention of hydrogen peroxide by this membrane, that is, failure to permit rapid passage of hydrogen peroxide from the immobilized enzyme to the electrode face can upset the equilibrium of the reaction and lead to erroneous results; it also can lower sample throughout and increase reagent usage.

The present invention by employing an electrode assembly having a first or outer membrane having a thickness of 1 to 20 $\mu$m, preferably 5 to 7 $\mu$m, and a pore size of 10 to 125 Å, which limits the diffusion of glucose molecules through the membrane, ensures the presence of sufficient oxygen in contact with the immobilized enzyme. Moreover, by providing a second or inner membrane having a thickness of 2 to 4 $\mu$m, more preferably 2 to 3 $\mu$m, the present invention provides sufficient permeability to ensure rapid removal of hydrogen peroxide from the enzyme into contact with the sensor electrode and rapid achievement of an equilibrium state.

In using the electrode of the present invention for assaying glucose, the electrode may be maintained in contact with the sample until the reaction attains equilibrium, after which an amperometric measurement is taken and compared with that of a standard solution taken under the same conditions, a procedure which requires of the order of 10 to 30 seconds. Additional time is required to wash residual sample from the outer face of the first membrane and allow the sensor electrode current to return to its base line value, so that in the case of an electrode used for successive assays of different samples, the total time for each sample is of the order of 60-80 seconds, depending upon the concentration of glucose.

In using the electrode of the present invention, in the conventional procedure of waiting for equilibrium to be established before measuring electrode current, the time required for assaying a succession of different samples is somewhat less than the time required using electrodes of the prior art. However, the electrode of the present invention has been found to make it possible to employ a different and much more rapid procedure, particularly beneficial in the case of samples having high glucose concentrations. It has been found that accurately reproducible assays can be achieved with the electrode of the present invention by making the amperometric measurement before reaction equilibrium has been achieved. Instead of waiting for equilibrium to be attained, the measurement is made at an arbitrary and standard time while the reaction in the cell is still approaching equilibrium. Preferably, the time of measurement is not less than 5 seconds after the sample is first brought into contact with the first or outer membrane. More preferably, to obtain the most reproducible results the time of measurement should be selected such that the current has achieved at least 90% of the steady state value. Contact of the sample with the membrane need not be thereafter continued, and preferably the sample is displaced as rapidly as possible by water or a buffer solution in order to return the electrode current to its base line value. This allows for a high throughput that is particularly advantageous when the analyzer containing the sensor has other sensors as well. Moreover, making the reading at such an early time has the advantage of limiting the effects of interfering substances, which generally take longer to move through the inner membrane than $H_2O_2$; thus, a good $H_2O_2$ reading is obtained with limited interference from the substances, which have yet to get through the membrane.

Alternatively, the electrode and its laminated membrane can be combined with a flow-through sample chamber or cell of limited size for presenting the sample to the face of the first membrane; the volume or size of the sample and the rate of flow can be so selected as to provide a standard short time of residence of the sample in contact with the outer membrane. In this embodiment, the sample is preferably of a fixed standard volume or size and is forced through the chamber across the face of the membrane via a peristaltic pump. Consequently, only a minimal quantity of sample, in the form of a thin surface film, remains in the chamber after passage of the specimen. This residual film of sample is rapidly consumed and can be rapidly removed by flowing through the chamber a small quantity of buffer, thus restoring the current to the base line value and readying the sensor for assay of a new sample.

Figure 1:
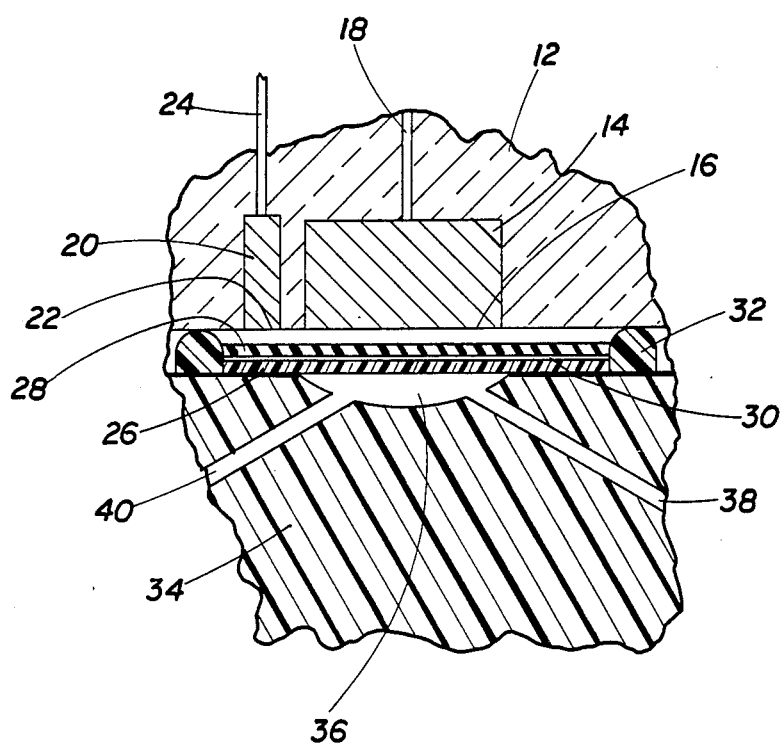
FIG. 1 is a view in section, partly broken away, showing one embodiment of the present invention including a flow chamber, on an enlarged scale.

As shown in FIG. 1 of the drawing, the electrode of the present invention comprises an electrically insulating support body 12 which may be of elongated cylindrical shape carrying at its end a platinum sensor electrode or anode 14 having an active or exposed face 16 and a conductor 18. The lower end of the support body 12 also carries a silver/silver chloride reference electrode 20 having an exposed face 22 and a conductor 24. Conductors 18 and 24 lead to an amperometer (not shown). Disposed across the exposed faces of the electrodes is a laminated membrane including a first or outer membrane 26 and a second or inner membrane 28 adhesively secured together by an intermediate layer 30 comprising the enzyme glucose oxidase, preferably a mixture of the enzyme and a cross-linking or binding agent such as glutaraldehyde. The laminated membrane is sealed in liquid-tight relation to the lower face of support body 12 by O-ring 32 or any other suitable means.

Membrane 26 is preferably polycarbonate but may consist of any other suitable solid porous or permeable material having a thickness of 1 to 20 $\mu$m, preferably 5 to 7 $\mu$m, and a pore size of 10 to 125 Å, more preferably 10 to 110 Å.

Membrane 28 may be of silicone rubber, methyl methacrylate or other suitable porous and permeable material, e.g., cellulose acetate butyrate, and preferably comprises cellulose acetate. It has a thickness of 2-4 $\mu$m, more preferably 2-3 $\mu$m.

In the embodiment shown, a flow cell 34 is mounted in liquid-tight relation against the lower face of outer membrane 26, being sealed thereto by a silicone washer or by O-ring 32. Cell 34 may be constructed of polystyrene, polymethacrylate, or any other suitable rigid liquid impervious material and includes a chamber 36 exposed to the face of membrane 26 as well as inlet 38 and outlet 40. In a preferred embodiment, the volume of chamber 36 together with inlet 38 and outlet 40 is approximately 5 to 10 microliters.

In operation, when outer membrane 26 contacts a sample of solution, glucose molecules and oxygen molecules present in the sample pass through it and contact the enzyme in layer 30; the enzyme catalyzes the oxidation of glucose to gluconic acid. The hydrogen peroxide produced during the oxidation passes through membrane 28 and contacts surface 16 of sensor electrode 14, which is poised at −700 mV in relation to reference electrode 20.

Cellulose acetate membrane 28, as pointed out above, has a thickness of 4 $\mu$m or less (more preferably between 2 and 3 $\mu$m). If membrane 28 is thicker than 4 $\mu$m, the passage of $H_2O_2$ through the layer is hindered or slowed. If the membrane is thinner than 2 $\mu$m, it will not be strong enough. Membrane 28, while permitting the quick passage of hydrogen peroxide, is a barrier to the passage of other low molecular weight substances (e.g., ascorbic acid, uric acid, salicylic acid) that may interfere with measurements made by anode 14; substances such as ascorbic acid and uric acid are often present in samples being analyzed and readily pass through polycarbonate membrane 26.

Membrane 26 is a 100 Å pore size straight pore polycarbonate film having a thickness of 1 to 20 $\mu$m (more preferably 5 to 7 $\mu$m) and having $6 \times 10^8$ pores/cm$^2$. Such films are available from Nuclepore Filtration Products of Pleasanton, Calif. The low pore size does not allow high molecular weight interfering and contaminating substances that may be present in a sample to pass through to the enzyme layer. Importantly, the 100 Å pore size is small enough to limit the diffusion of glucose molecules into enzyme layer 30. If the diffusion of glucose molecules is not so limited, sufficient oxygen may not reach enzyme layer 30 to oxidize all of the glucose molecules that have diffused through layer 26, leading to inaccurate glucose measurements. A diffusion-limiting pore size is especially important where the sample is undiluted blood or serum, which frequently has a relatively high glucose concentration. A pore size of 150 Å does not sufficiently limit the diffusion of glucose molecules to allow glucose measurements to be made on undiluted serum, plasma, whole blood, or urine. The lower limit on pore size that may be used is that size which does not allow any substantial amount of glucose molecules to diffuse through (about 10 Å diameter).

The diffusion of glucose through a membrane can be quantified in terms of molar flux. A membrane will sufficiently limit the diffusion of glucose if that membrane has a pore size (diameter) that limits the molar flux of glucose molecules to less than 60% the molar flux of glucose through a membrane having the same pore density and thickness but having a pore size of 150 Å; such a limitation is obtained if the pore size is no greater than 125 Å. More preferably, the molar flux of glucose should be less than 40% the molar flux of glucose in a membrane having the same pore density and thickness but having a 150 Å pore size; such a limitation is obtained if the pore size is no greater than 110 Å.

Glucose oxidase layer 30 most preferably is a mixture of the enzyme and a cross-linking agent such as glutaraldehyde.

The procedure for preparation of the laminated membrane is described in Newman, U.S. Pat. No. 4,073,713, which is hereby incorporated by reference.

In general, in preparation of the laminated membrane cellulose acetate is dissolved in 23:1 cyclohexanone:isopropanol, and the solution is deposited onto water. A cellulose acetate film forms, which is picked up by a polyethylene carrier sheet. An enzyme-glutaraldehyde liquid is placed on the cellulose acetate layer, and a polycarbonate film is brought into contact with the enzyme preparation on the cellulose acetate layer to form a laminate, which is pressed by a roller to insure confluency and minimize thickness. Crosslinking by the glutaraldehyde forms an immobilized enzyme layer. The laminate is dried by allowing it to sit in air at room temperature for a half-hour or more. The carrier sheet is removed to give a laminate ready for installation into an electrode assembly of a polarographic cell.

In a typical assay, a sample of the solution is flowed through the inlet 38 and fills the flow chamber 36. The diffusion of glucose and oxygen and resultant hydrogen peroxide formation have previously been described. As the hydrogen peroxide solution contacts the surface 16 of anode 14, in the embodiment shown, it also contacts the face 22 of reference electrode 20, forming an electroconductive path between the two electrodes. A current between the two electrodes is generated, the magnitude rising to a constant (steady state) value related to the equilibrium concentration of the hydrogen peroxide.

Figure 2:
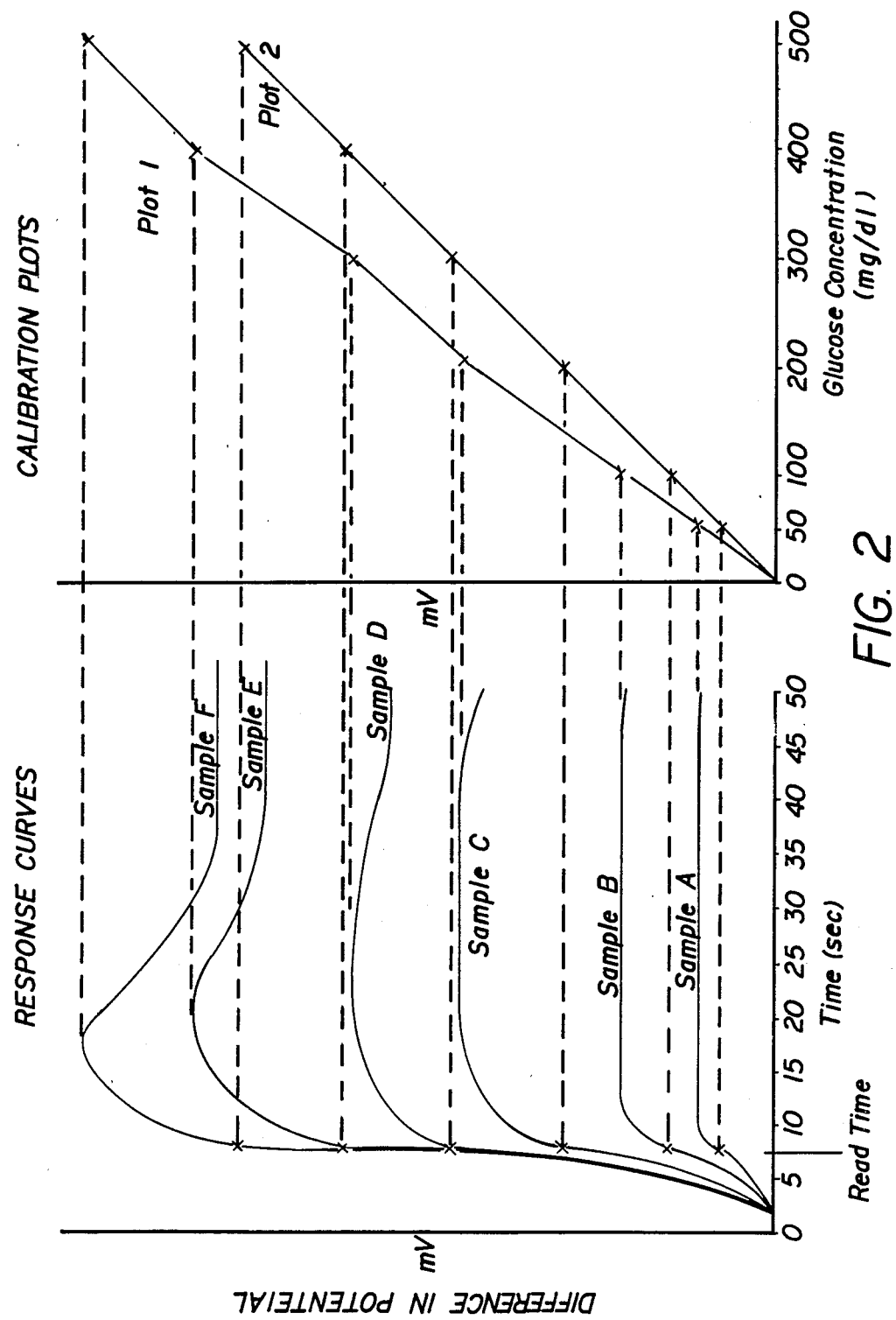
FIG. 2 shows amperometric response curves of the present invention for samples of varying glucose concentration when the reaction is allowed to proceed to equilibrium.

Typical response curves are shown in FIG. 2. In this figure, the current is plotted against time in seconds, from the beginning of the sample cycle (the time at which the sample contacts the outer membrane 26) in the left-hand portion of the plot for Samples A–F having glucose concentrations of 50, 100, 200, 300, 400 and 500 mg/dl respectively. As is shown, the current output rises sharply shortly after the sample cycle starts. The rise corresponds to the increasing number of glucose molecules that diffuse and react in the enzyme layer. Fairly quickly the glucose supply equilibrates, resulting in a steady supply and consumption of glucose molecules, and the reaction proceeds, reaching equilibrium (at which the current becomes constant) after about 8, 12 and 20 seconds in the case of samples A, B, and C respectively. In the steady state the current is directly proportional to the concentration of glucose in the sample, as shown by calibration plot 1 in the right-hand portion of FIG. 2. In the case of samples D, E, and F, having glucose concentrations of 300, 400 and 500 mg/dl respectively, equilibrium is only approached momentarily, if at all, even when the electrode assembly of the present invention is employed, because the rate of diffusion of glucose into the glucose oxidase layer 30 is too high for the available supply of oxygen. As a result Calibration Plot 1, the standard against which unknown samples are compared when assayed by this procedure, becomes slightly non-linear at high concentrations of glucose, such as those which may be encountered in undiluted whole blood or serum, and therefore of somewhat decreased accuracy.

By making the measurements of current difference for each sample at the same fixed time of 7.5 seconds after initial contact of the sample with the outer face of membrane 26, as is also shown in FIG. 2, there is obtained Plot 2 as the calibration plot. This calibration plot is completely linear to concentrations above 500 mg/dl, ensuring high accuracy, despite the fact that each measurement is made before equilibrium is attained.

The procedures described above can be carried out either by simply immersing the exposed face of outer membrane 26 in a pool of the sample solution to be assayed, or by sealing the flow cell 34 to the face of the membrane and flowing a sample through chamber 36 for as long as necessary. In using the flow cell, when measurement is made within 5 to 10 seconds after initial contact of the sample solution with membrane 26, washing of residual sample from chamber 36 with appropriate buffer can be immediately begun to prepare the electrode assembly for the next sample. Total time for each sample measurement is less than 45 seconds under such conditions.

Figure 3:
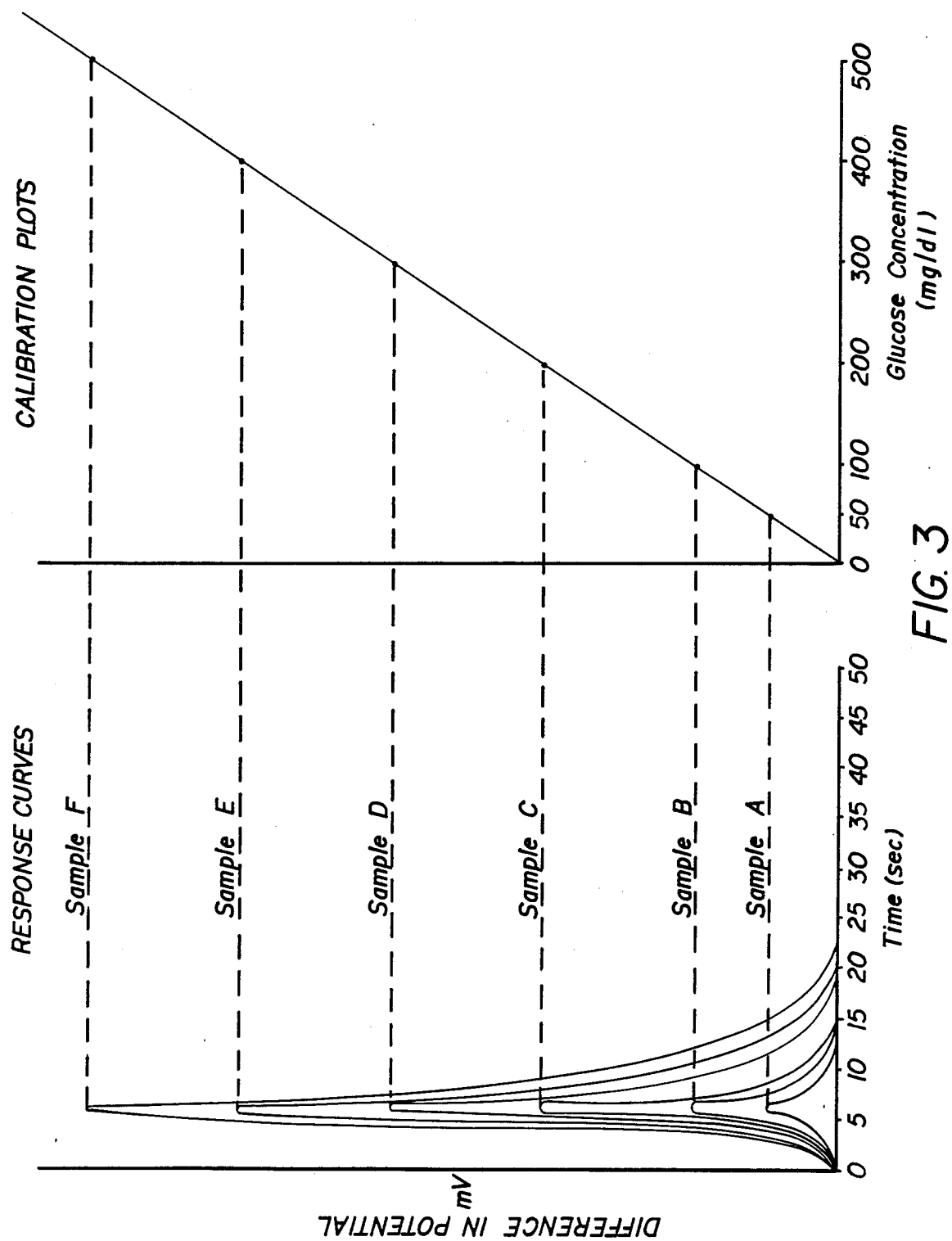
FIG. 3 shows the response curves obtained when flowing samples of restricted size past the electrode of the present invention.

An alternative method which can be used when flow cell 34 is in place is to provide a specimen of the sample liquid which is limited in volume, for example, two to ten times the total volume of the chamber 36, and the specimen is pumped through the cell and past the electrode. The residual film on membrane 36 produces a peak current proportional to the glucose concentration; the peak current is lower than the current that would be obtained had a steady state been reached. In practice the dwell time of the sample specimen in chamber 36 can be of the order of 3 to 10 seconds. Plots of response curves of the same standard solutions made under these conditions at a specimen dwell time of 5 seconds in each case (chamber volume 10 μl) are shown in FIG. 3. As can be seen, in each case the potential peaked sharply at 6–8 seconds after initial contact and before equilibrium was achieved, and the peaks, as shown by the calibration plot, were precisely proportional to glucose concentration. Consequently, this procedure of measuring maximum current produces a linear calibration plot and highly accurate results at concentrations even higher than 500 mg/dl. Since the specimen is immediately followed by air, and very little unreacted specimen remains, little washing with buffer is required to prepare the electrode assembly for assay of the next sample specimen and the total time for measurement of each sample specimen is of the order of 30 seconds or less.

Calibration plots made as described above for each electrode assembly are then used as the standard of comparison for assays of unknown samples carried out in the same protocol, in the usual manner.

What is claimed is:

1. An electrode assembly for use in a polarographic cell for assay of glucose in solution, said assembly comprising a reference electrode and a sensor electrode having a laminated membrane covering the solution-contacting face of said sensor electrode,
   in which said laminated membrane comprises
   an outer solution-contacting membrane from 1 to 20 μm thick having a pore size of 10 to 125 Å,
   an inner membrane adjacent the face of said sensor electrode from 2 to 4 μm thick, and
   an adhesive glucose oxidase layer between said membranes holding them together,
   said inner membrane having a permeability sufficiently great to ensure passage of hydrogen peroxide from said glucose oxidase layer to the face of said sensor electrode.

2. An electrode assembly as claimed in claim 1 in which said outer membrane comprises polycarbonate.

3. An electrode assembly as claimed in claim 2 in which said inner membrane comprises cellulose acetate.

4. An electrode assembly as claimed in claim 3 comprising in addition a flow cell for directing a sample of said solution past the exposed face of said outer electrode, said cell being sealed to said face and having a chamber exposed to said face, and an inlet and an outlet for said chamber, said chamber, inlet and outlet having a fixed volume.

5. An electrode assembly as claimed in claim 2 comprising in addition a flow cell for directing a sample of said solution past the exposed face of said outer electrode, said cell being sealed to said face and having a chamber exposed to said face, and an inlet and an outlet for said chamber, said chamber, inlet and outlet having a fixed volume.

6. An electrode assembly as claimed in claim 1 in which said inner membrane comprises cellulose acetate.

7. An electrode assembly as claimed in claim 6 comprising in addition a flow cell for directing a sample of said solution past the exposed face of said outer electrode, said cell being sealed to said face and having a chamber exposed to said face, and an inlet and an outlet for said chamber, said chamber, inlet and outlet having a fixed volume.

8. An electrode assembly as claimed in claim 1 comprising in addition a flow cell for directing a sample of said solution past the exposed face of said outer electrode, said cell being sealed to said face and having a chamber exposed to said face, and an inlet and an outlet for said chamber, said chamber, inlet and outlet having a fixed volume.

9. The method of assaying glucose in solution which comprises bringing a sample of said solution into contact with the outer membrane of an electrode assembly as claimed in any of claims 1, 2, 6 or 3, measuring the current between said electrodes at a time at least as great as 5 seconds after initial contact and substantially less than the time required for the current to become constant, and comparing the measured current with that of a standard solution containing a known concentration of glucose measured under identical conditions.

10. The method of assaying glucose in solution which comprises flowing through the flow cell of an electrode assembly as claimed in any of claim 8, 5, 7 or 4 a sample of said solution, measuring the maximum current between said electrodes at a time at least as great as 5 seconds after initial contact and substantially less than the time required for the potential to become constant, and comparing the measured maximum current with that of a standard solution containing a known concentration of glucose measured under identical conditions, said sample having a fixed volume greater than the volume of said chamber and inlet, and said rate of flow being such that all of said sample except for residual liquid film is passed through said chamber before said measured current has become constant.

* * * * *